United States Patent [19]

Lee

[11] 4,454,886

[45] Jun. 19, 1984

[54] EEG WITH AUDIO OUTPUT

[76] Inventor: Arnold S. J. Lee, 1033 Hilts Ave., Los Angeles, Calif. 90024

[21] Appl. No.: 301,934

[22] Filed: Sep. 14, 1981

[51] Int. Cl.³ .............................................. A61B 5/04
[52] U.S. Cl. ................................................... 128/732
[58] Field of Search ............... 128/732, 905, 731, 733; 360/8; 369/60

[56] References Cited

U.S. PATENT DOCUMENTS

| | | | |
|---|---|---|---|
| 3,110,770 | 11/1963 | Howell | 128/715 X |
| 3,753,433 | 8/1973 | Bakerich et al. | 128/732 |
| 3,882,850 | 5/1975 | Bailin et al. | 128/732 |
| 3,890,957 | 6/1975 | Freeman | 128/732 |
| 4,020,291 | 4/1977 | Kitamura et al. | 360/8 X |

Primary Examiner—Kyle L. Howell
Assistant Examiner—John C. Hanley
Attorney, Agent, or Firm—Freilich, Hornbaker, Rosen & Fernandez

[57] ABSTRACT

A method is described for generating sounds (which are of a musical nature) that are related to the state of a person's brain, which is useful in anesthesiology and other applications. A brain wave signal, which may be derived from an electroencephalograph, is converted in real time from an analog to a digital signal, and stored in a memory. An epoch delineator detects points along the signal which can define segments of the signal. The signals in the memory are read out in segments, with the segment signals repeatedly read out N number of times and at a rate N times faster than the input rate to the memory, to generate a train of signals that are high frequency replicas of the segment. Thus, the multiple replicas of the segment are all read out during the same time period required to originally store the segment, and after each segment is read out the next segment to be stored is repeatedly read out. In one system, a segment ends when the filtered brainwave signal crosses a zero voltage level in a positive-going direction.

11 Claims, 4 Drawing Figures

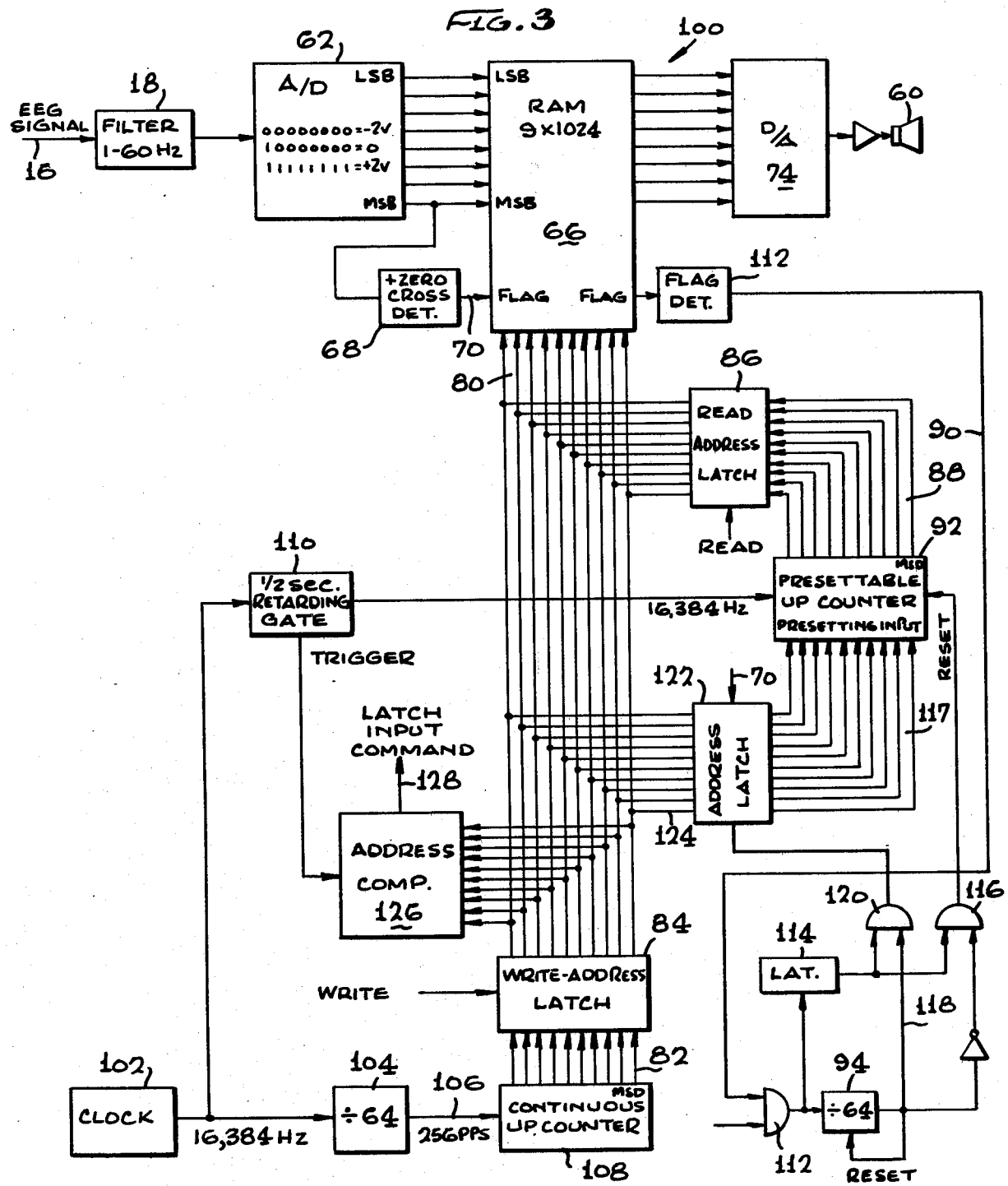
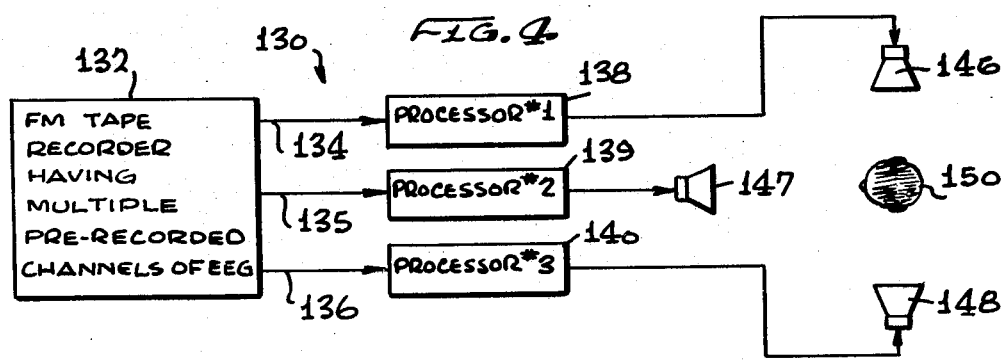

EEG WITH AUDIO OUTPUT

BACKGROUND OF THE INVENTION

Knowledge as to the state of a person's mind is useful in several applications. In anesthesiology, the anesthesiologist typically administers a light anesthesia to make the patient sleep, administers a narcotic to prevent the patient from waking up from the pain that would otherwise arise from an operation, and administers a drug that relaxes or paralyzes the patient to prevent his muscles from reacting to stimulation from the operation procedure. In this situation, it is often found useful to detect the patient's brainwaves as by use of an electroencephalograph and to apply the brainwaves to a Fourier analyzing device that shows the amplitude of various frequencies present in the brainwaves. Both the encephalograph and the display on the Fourier analyzing device are less than satisfactory for detecting the state of the patient's brain because it is difficult to interpret such displays. A technique for providing an output representing the brainwaves of a person, which facilitated their interpretation, would be of great value to the anesthesiologist. Such an output would also be useful in biofeedback practices, for aiding in body control, or for entertainment purposes.

SUMMARY OF THE INVENTION

In accordance with one embodiment of the present invention, a method is provided for generating an output signal that is highly indicative of the state of a person's brainwave functioning. The method includes generating an input signal representing the brainwave or EEG (electroencephalograph) of a patient, and selecting sequential segments of the signal. A sound output signal is then generated which consists of a sequence of output segment signals, each having substantially the same duration as a corresponding input segment of the input signal. However, each output segment signal comprises a large number N of replica signals in sequence, with each replica signal having a duration of 1/N times the duration of the output segment signal (and of the corresponding input segment), and with each replica signal having a waveform which is geometrically similar to the waveform of the corresponding input segment of the brainwave-representing signal. In one example, an input segment which happens to be of one second duration, is used to generate 64 replica signals in sequence, with each replica signal having a duration of 1/64th second, and with each replica signal having a waveform similar to that of the entire input segment.

In one embodiment of the invention, an epoch or segment detector, detects the instant when the brainwave-representing input signal is zero in a positive-going direction, and uses this as the end of one segment and the beginning of the next.

The novel features of the invention are set forth with particularity in the appended claims. The invention will be best understood from the following description when read in conjunction with the accompanying drawings.

BRIEF DESCRIPTION OF THE DRAWINGS

FIG. 3 is a more detailed block diagram of the system of FIG. 2.

FIG. 4 is a simplified block diagram view of a system which uses circuits of the type shown in FIG. 2.

DESCRIPTION OF THE PREFERRED EMBODIMENT

Figure 1:
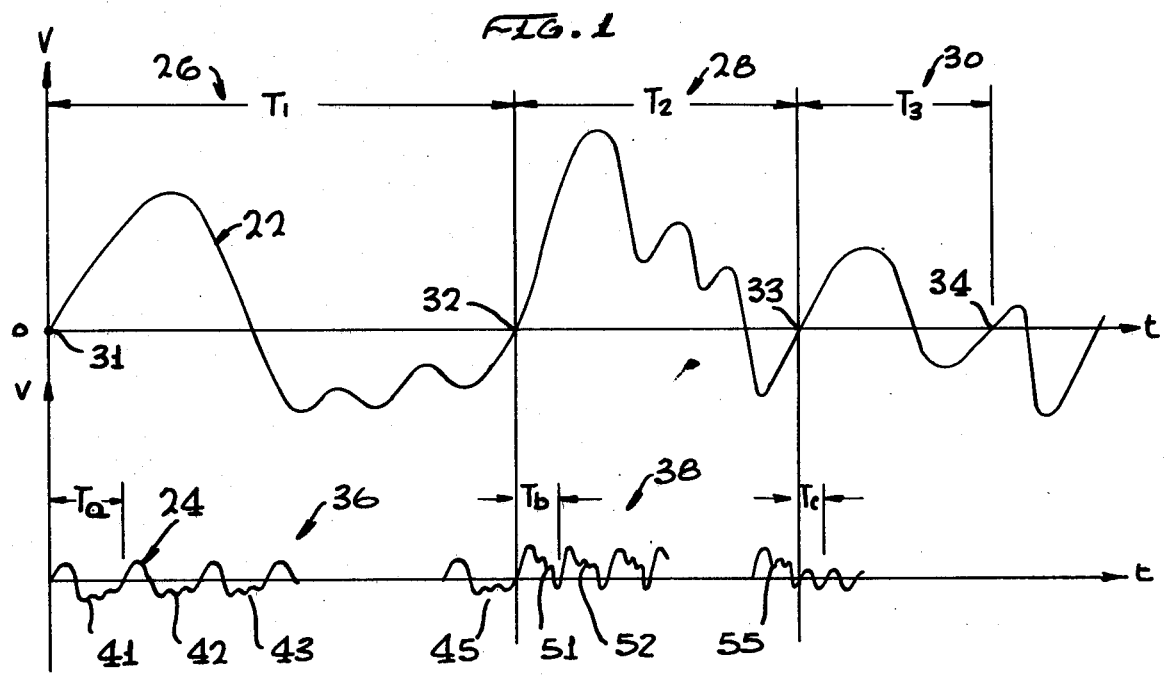
FIG. 1 is a graph showing wave forms of an EEG signal and of a sound output signal produced by one embodiment of the method of the invention.
Figure 2:
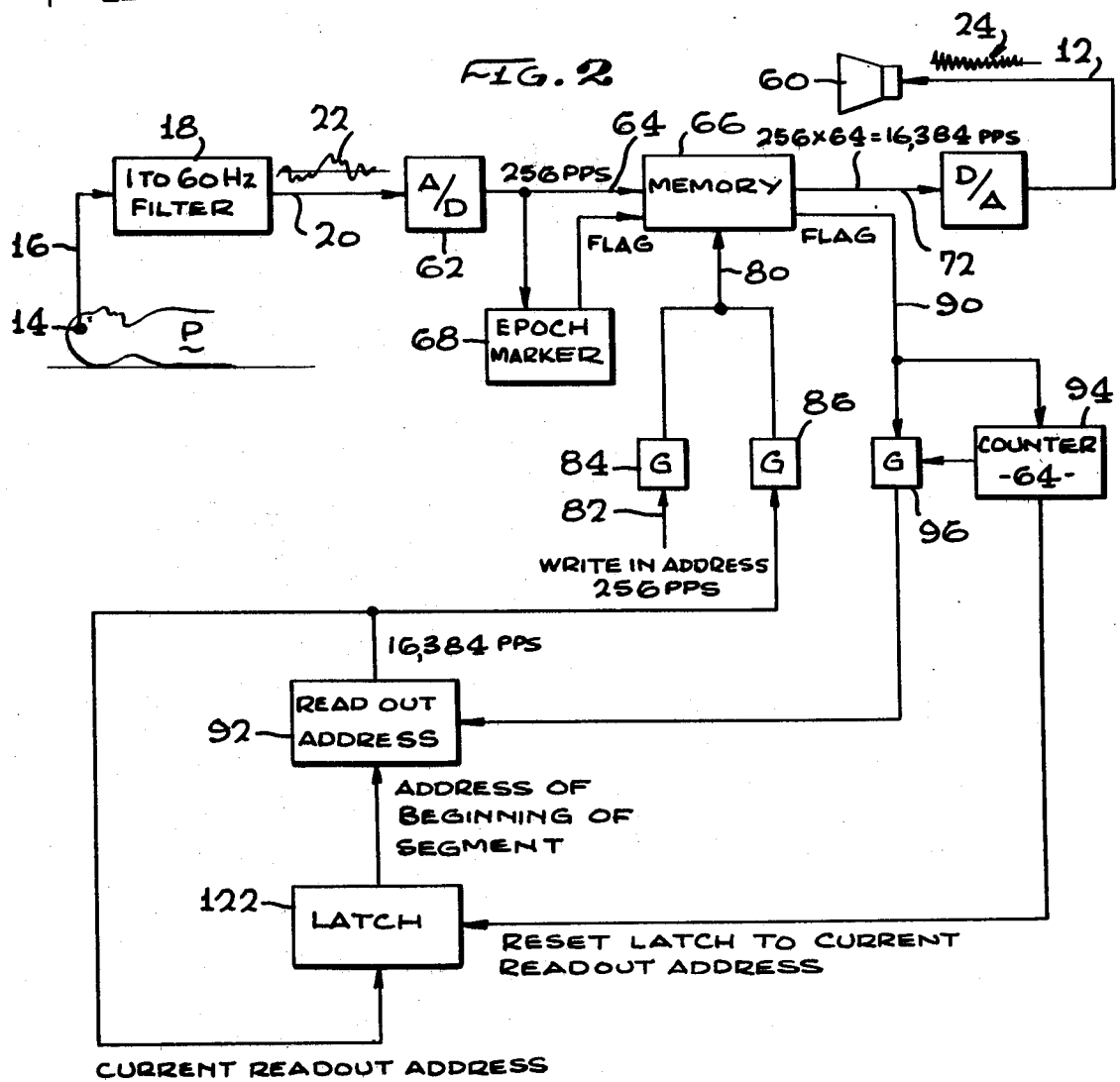
FIG. 2 is a simplified block diagram view of a system of the invention which produces the waveforms of FIG. 1.

FIG. 2 illustrates a system 10 of the present invention, which produces a sound output signal on a line 12 which indicates the state of the brainwaves of a person P. An electrode 14 coupled to the head of the person produces an output on line 16 representing the brainwaves of the person along with considerable noise. Since the usual brainwave frequencies of interest are those lying in a band on the order of 1 to 50 Hz, the initial signal produced from the electrode is passed through a band-pass filter 18 which excludes noise lying considerably out of the band of interest. A portion of a typical output on line 20 is shown in the graph 22 of FIG. 1, the portion shown in the graph lasting a few seconds. The system processes the filtered brainwave signal 22, and generates a sound output signal shown in the graph 24, which is designed to be fed to a loudspeaker for hearing by an interested person such as an anesthesiologist who is monitoring the brain functioning of the person generating the brainwave.

In order to generate the sound output signal from the filtered brainwave 22, the brainwave signal is first analyzed to divide it into epochs, or segments, such as those shown at 26, 28 and 30 of durations $T_1$, $T_2$ and $T_3$. This is accomplished by detecting the points such as 31-34 at which the brainwave signal 22 crosses zero in a positive-going direction. In FIG. 1, it may be assumed that the first segment 26 has a duration $T_1$ which happens to be one second. The output signal 24 has a corresponding output segment 36 of the same duration $T_1$ as the input segment. However, the output segment 36 includes a train of replica signals 41, 42, 43, etc. up to the last 45, which are identical to one another and which are each similar to the input segment 26 of the filtered brainwave signal. In a system wherein there are sixty-four replica signals such as 41, 42, etc. in each output segment 36, and where the duration $T_1$ of the input and output segments in one second, each replica signal such as 41 has a duration Ta of 1/64th second. The entire train of sixty-four replica signals has a duration of one second. When the signals are displayed as a graph of voltage vs. time, and the voltage of the output signal 24 is reduced in an appropriate amount, each replica signal such as 41 or 42 will be geometrically similar to the entire input segment 26 of the brainwave signal 22. That is, if the display of one replica signal 41 is magnified, it will be geometrically congruent to the input segment 26.

In FIG. 1, it is assumed that the second input segment 28 has a duration $T_2$ of 0.6 seconds. The corresponding output segment 38 has sixty-four replica signals 51, 52, etc. to 55, which all have a duration Tb of 1/64th of 0.6 seconds.

It is found that when the output signal 24 is delivered to a loudspeaker such as 60 of FIG. 2, the resulting sound is interesting as well as entertaining, and the person hearing it can identify patterns in the sound. A typical sound has segments primarily in the range of 1/40th to 2 seconds duration each, with each segment containing a fundamental tone and harmonics. The fact that each segment includes a short replica repeated many times, such as sixty-four times, results in a definite tone being heard it is desireable that the number N of replica signals in each output segment signal be more than 10, for most of the output signals, so that an identifiable tone can be heard. Since the signal was filtered to minimize frequencies above 60 Hz, and the segments are of short duration there are a limited number of harmonics of the fundamental tone in each segment, and yet each segment usually has some harmonics to give it an identifiable characteristic.

A particular algorithm used to determine the boundaries of each epoch or segment, which uses each positive-going (or negative-going), zero (or other voltage) crossing, facilitates the creation of an output with minimal noise-like disturbances. In more general terms, the algorithm detects locations of the filtered brainwave signal which cross a predetermined level (such as zero volts) in a particular level-changing direction (either increasing or decreasing).

In the system of FIG. 2, the filtered brainwave signal on line 20 is delivered to an analog-to-digital converter 62, which samples the analog signal 22 and delivers an output on line 64 at a rate of 256 pps (pulses per second). This output is stored in a random access memory 66. The digital signals on line 64 representing the brainwave input signal, is also monitored by an epoch marking circuit 68, which detects each positive-going zero crossing. The output of the epoch marker is delivered over line 70 to the memory 66 as an additional bit to the memory input, with the bit being "1" whenever an epoch event, such as a positive-going zero crossing, is detected. The signals stored in the memory 66 are read out through line 72.

Each epoch or segment stored in the memory 66 is read out repeatedly, a total of sixty-four times, and at a rate sixty-four times as fast as the signal was initially entered into the memory. Thus, where a signal is entered into the memory over line 64 at 256 pps, it is read out over line 72 at a rate of 16,384 pps. As a result, it requires the same time to read out each segment sixty-four times as it does to originally enter the segment, so that the memory 66 has to be great enough to contain at least two longest segments. The output of the memory over line 72 is passed through a digital-to-analog converter 74, whose output 24 on line 12 is referred to herein as a sound output signal, in that it is intended to be used to drive a loudspeaker or the like, or an audio frequency recorder, to generate sounds and/or recordings. The sound output signal on line 12 can be connected directly to a loudspeaker 60, or in some cases, can be delivered to a recorder for later reproduction.

The addressing of the random access memory 66 for both the input signal on line 64 and the output signal on line 72, can be accomplished by alternating the address delivered over line 80 to the memory. A write-in address is delivered over a line 82 through a gate 84 to the address input 80 of the memory, at a rate of 256 pps, and which is synchronized with the analog-to-digital converter 62. In between each write-in address pulse on line 82, a gate 86 is opened (and gate 84 is closed) to deliver a readout address sixty-four times from line 88 to the memory. The readout address cycles sixty-four times through the same series of address members that define a segment, before beginning the address of the next segment. The flag, delivered over line 90 as one bit of the output from the memory, indicates the end of each segment, to reset the circuit 92 to the beginning of the segment. A latch 122 holds the address of the beginning of the segment, to determine the address to which the circuit 92 is reset at every flag detection. A counter 94 counts the number of flag signals, and when sixty-four of such flag signals have been received, it closes a gate 96 to prevent the resetting of the address circuit 92, and instead delivers a reset signal over line 95 to the latch 122. The latch 122 is then reset to the last address on line 88 (which is the end of the last segment and the beginning of the new one to be read out.)

FIG. 3 is a more detailed block diagram of the circuit of FIG. 2. The circuit 100 shown in FIG. 3 includes an oscillator or clock 102 which generates an output of 16,384 Hz, which passes through a divider 104 that divides it by sixty-four, to deliver a write clock signal on line 106, of 256 pps. The write clock signal on line 106 is delivered to a 10-bit binary counter 108 whose output 82 carries a count that advances to 1024 every four seconds and then begins at zero again. This count passes through a gate or latch 84 to the address input 80 of the memory 66.

The 16,384 pps signal from clock 102 is also delivered through a gate 110 to a presettable counter 92. The gate 110 automatically shuts off for one-half second when the apparatus is turned on to provide time for at least part of a first segment to enter the memory. The presettable binary counter 92 determines the readout address for the memory. The output of the counter 92 is delivered over line 88 and through a latch or gate 86 to the address input 80 of the memory. Whenever a flag signal leaves the memory 66, and is detected by a flag detector 112, a pulse is delivered over line 90. This pulse is delivered through an AND gate 112 to a latch circuit 114 that delivers a signal through a gate 116 to the counter 92, to reset the count therein to whatever count is on the preset input 117 of the counter. The input 117 is the address of the beginning of the segment that has just been read out, so that the readout address delivered to the memory 66 is controlled to read out the same segment again and again.

The flag signal on line 90 is also delivered to the sixty-four counter 94. When the counter 94 has received sixty-four flag signals, it delivers an output over line 118 through a gate 120 to a latch circuit 122. The latch circuit 122 then delivers a new preset input on line 114 to the counter 92, which equals the address of the beginning of the next segment. The addresses of the beginning of subsequent segments are stored in the latch circuit 122. The input 124 to the latch circuit is the write address which existed at the last time a flag was delivered from the epoch detector 68 to the memory 66. In order to safeguard against the possibility that the read and write addresses might coincide, a comparator circuit 126 is provided which compares the output of the write address latch 84 with the last previous output of the read address latch 86. If the comparison shows that the addresses are the same, then the comparator delivers a signal over line 128 to delay the read address by one-half second.

While the above description refers to a single channel of brainwaves, it is useful to detect and process brainwaves detected at two or more different locations or times. The two or more processed signals can be played simultaneously to enable the listener to compare them. FIG. 4 illustrates a system 130 which includes a tape recorder 132 which can reproduce multiple channels of brainwaves simultaneously on lines such as 134–136, Three signal processing circuits 138-140 of the type shown in FIG. 2 generate outputs on lines 142-144 of the type shown at 24 in FIG. 1. The outputs drive three speakers 146-148. A listener 150 hears all three speakers simultaneously.

As discussed above, the algorithm for determining the beginning and end of each epoch or segment, based upon detecting the positive-going zero crossing of the filtered brainwave signal, provides a relatively simple technique for producting a pleasant and informative sound output signal. The segments last long enough, such as primarily between one-tenth second and two seconds, to enable the listener to hear a particular tone while being short enough for the listener to detect patterns of segments, with each segment having primarily a basic tone with a number of overtones and with minimal noise caused by the transition between segments, each at its particular intensity. The zero crossing detection enables the end of each replica signal such as 41 to match the voltage at the beginning of the next replica signal such as 42, and also enables the end of the last replica signal such as 45 of a segment to match the beginning replica signal such as 51 of the next segment. However, other algorithms can be utilized to determine the beginning and end of an epoch or segment into which the brainwave signal is to be divided and then reproduced at high speed and many times. For example, points along the filtered brainwave signal where it reaches a minimum and then increases, or in other words at points where the derivative is zero and afterwards increases, can be used to define the end of a segment, so long as provisions are made to match the beginnings and ends of each replica and each segment. It should also be understood that the method of the invention can be implemented not only by hard wired circuits, but also by proper programming of a computer. The invention is useful for indicating the state of a person's brainwaves for medical purposes such as to aid an anaestheseologist. It is also useful for self-help purposes such as biofeedback and for entertainment purposes because of the interesting sounds that are created, the moods which they evoke and the moods which they create.

Although particular embodiments of the invention have been described and illustrated herein, it is recognized that modifications and variations may readily occur to those skilled in the art and consequently it is intended that the claims be interpreted to cover such modifications and equivalents.

What is claimed is:

1. A method for generating a sound output signal representing a brainwave comprising:
    establishing a first signal representing a brainwave;
    selecting a multiplicity of sequential brainwave segments of said first signal, each brainwave segment lasting for a particular duration; and
    generating a sound output signal comprising a series of output segment signals, each output segment signal comprising a plurality of replica signals in sequence wherein each replica signal has a duration which is a fraction of the duration of a corresponding segment of the first signal, and wherein each replica signal is a waveform which is substantially geometrically similar to the waveform of the corresponding segment of the first signal.

2. The method described in claim 1 wherein:
    each output segment signal has substantially the same duration as a corresponding segment of said first signal, each output segment signal comprises a predetermined number N of replica signals, and each replica signal has a duration of substantially 1/N times the duration of the output segment signal and of the corresponding segment of the first signal.

3. The method described in claim 1 wherein:
    said step of selecting includes detecting locations of said first signal which cross a predetermined level in a predetermined level-changing direction.

4. The method described in claim 3 wherein:
    said predetermined level is zero and said predetermined direction is the positive-going direction.

5. The method described in claim 1 wherein:
    the number N of replica signals in each output segment signal is more than ten, whereby to provide enough repetitions to provide an identifiable tone for each train of replica signals which last the period of a segment.

6. A method for generating a sound output signal representing a brainwave comprising:
    establishing an analog first signal representing the filtered electroencephalograph of a person;
    converting said analog first signal into digital signals at a constant rate;
    storing said digital signals in a memory; and
    reading out the digital signals stored in said memory, in segments, including repeatedly reading out the same segment a predetermined number N of times, with the period during which each segment is read out being 1/N times the period of time during which the signals representing the segment were stored in said memory, and then repeatedly reading out the segment which was next stored in the memory.

7. The method described in claim 6 wherein;
    the beginning of each segment occurs at a location corresponding to the analog first signal passing a predetermined value in a predetermined direction, the term "direction" including the situation when the signal is increasing and the situation when the signal is decreasing but the term "predetermined direction" including only one of such situations, whereby to provide a moderately smooth transition between read out segments.

8. A method for processing an EEG signal representing brainwaves, comprising:
    detecting locations along said signal which cross a predetermined magnitude in a predetermined direction, with two of such detections, one occurring after the other, representing an input segment; and
    generating a sound output signal which includes a plurality of output segments, each output segment including multiple identical replica signals in sequence, each replica signal having a waveform which is similar in form to a corresponding input segment, but each replica signal has a duration which is a fraction of the duration of the corresponding input segment.

9. Apparatus for processing an EEG signal representing a brainwave, comprising:
    means for establishing a first signal representing a brainwave;
    means responsive to said first signal for defining segments of said first signal; and
    means for generating a sound output signal comprising a series of output segments that each comprise a plurality of replica signals in sequence, wherein each replica signal has a duration which is a fraction of the duration of a predetermined segment of the input signal, and wherein each replica signal has a waveform which is geometrically similar to the waveform of the predetermined segment of the first signal.

10. The apparatus described in claim 9 wherein:
said generating means generates output segments that are such of the same duration as a corresponding segment of said first signal, with each output segment signal comprising a predetermined number N of replica signals, and with each replica signal having 1/N times the duration of the output segment signal and of the corresponding segment of the input signal.

11. The apparatus described in claim 9 wherein:
said means for defining segments include a circuit responsive to the magnitude of the first signal reaching a predetermined magnitude which is substantially of zero magnitude at a time when the first signal is changing in a predetermined direction which is either increasing or decreasing.

* * * * *